United States Patent [19]
Goodwin et al.

[11] Patent Number: 5,817,061
[45] Date of Patent: Oct. 6, 1998

[54] TROCAR ASSEMBLY

[75] Inventors: Matthew S. Goodwin, Cincinnati, Ohio; Michael A. Murray, Bellevue, Ky.

[73] Assignee: Ethicon Endo-Surgery, Inc., Cincinnati, Ohio

[21] Appl. No.: 857,433

[22] Filed: May 16, 1997

[51] Int. Cl.$^6$ ........................... A61M 5/18
[52] U.S. Cl. ................. 604/164; 604/272; 600/121
[58] Field of Search ................. 604/158, 164, 604/166, 168, 264, 272; 606/15–16, 14; 607/93; 600/101, 114, 121, 129, 136

[56] References Cited

U.S. PATENT DOCUMENTS

| | | | |
|---|---|---|---|
| 3,437,747 | 4/1969 | Sheldon | 600/129 |
| 4,535,773 | 8/1985 | Yoon | 604/51 |
| 4,601,710 | 7/1986 | Moll | 604/165 |
| 5,144,942 | 9/1992 | Decarie et al. | 128/4 |
| 5,256,147 | 10/1993 | Vidal et al. | 604/158 |
| 5,256,149 | 10/1993 | Banik et al. | 604/164 |
| 5,271,380 | 12/1993 | Riek et al. | 128/4 |
| 5,380,291 | 1/1995 | Kaali | 604/164 |
| 5,383,860 | 1/1995 | Lau | 604/167 |
| 5,405,328 | 4/1995 | Vidal et al. | 604/158 |
| 5,431,151 | 7/1995 | Riek et al. | 604/164 |
| 5,441,041 | 8/1995 | Sauer et al. | 600/106 |
| 5,453,094 | 9/1995 | Metcalf et al. | 604/164 |
| 5,496,280 | 3/1996 | Vanderbroek et al. | 604/167 |
| 5,549,565 | 8/1996 | Ryan et al. | 604/167 |
| 5,569,291 | 10/1996 | Privitera et al. | 606/185 |
| 5,591,192 | 1/1997 | Privitera et al. | 606/185 |
| 5,662,588 | 9/1997 | Lida | 600/121 |
| 5,685,820 | 11/1997 | Riek et al. | 600/114 |

FOREIGN PATENT DOCUMENTS 556056  8/1993  European Pat. Off. ............... 604/264

*Primary Examiner*—Ronald Stright
*Assistant Examiner*—Sharon Finkel
*Attorney, Agent, or Firm*—Matthew S. Goodwin

[57] ABSTRACT

A multi-patient use trocar assembly is disclosed. The trocar assembly has obturator and cannula subassemblies. The obturator subassembly has an elongated obturator shaft which can receive an endoscope at its distal end. The obturator shaft is reusable for multi-patient use. A transparent obturator tip is detachably mounted onto the end of the obturator shaft. The obturator tip is transparent and disposable. Because it is transparent, illuminated images provided by the endoscope within the body cavity can be transmitted through the obturator tip. Once the trocar assembly is used on a first patient, the obturator tip is detached and disposed of, and replaced with another obturator tip. Hospital costs are reduced because the trocar assembly can be reused multiple times, and only the obturator tip needs to be disposed of after each patient use.

16 Claims, 7 Drawing Sheets

TROCAR ASSEMBLY

BACKGROUND OF THE INVENTION

This invention relates to a trocar assembly for providing access to a surgical site within a body cavity during a minimally invasive surgical procedure. More particularly, it relates to a trocar assembly which has a long, reusable obturator shaft and a disposable obturator tip which can be attached and detached from the obturator shaft to enable multi-patient use of the trocar assembly.

Trocars have been available for providing access to a surgical site within a body cavity of a patient for a significant period of time. Of critical importance in the operation and use of trocars are the safety features of the trocar which minimize or prevent inadvertent puncture of body tissues or organs during initial penetration through the body wall. U.S. Pat. No. 4,535,773 describes numerous illustrations of trocars which have a shield to cover the sharp obturator tip when penetration of the body wall is completed. In a similar fashion, U.S. Pat. No. 4,601,710 describes a trocar where a shield is mounted concentrically around the obturator tip to cover the tip after the body wall has been penetrated. The '710 patent also states that the piercing tip can be adapted to be removable from the shaft.

Another type of trocar which is designed to minimize or prevent inadvertent puncture of body tissue during penetration is described in U.S. Pat. No. 5,271,380. The '380 patent describes a trocar which has a transparent obturator tip. Fiber optic cables are contained within the obturator shaft to provide illumination of the operative site and transmission of illuminated images through the transparent obturator tip to enable the user to visualize the penetration of tissue layers as the trocar is being used. Accordingly, a shield to cover the obturator tip of the trocar is unnecessary.

Another trocar which provides visualization during penetration is described in U.S. Pat. No. 5,380,291. The '291 patent describes a trocar with an obturator which has a hollow shaft for receiving an endoscope, and a transparent obturator tip for transmitting illuminated images provided by the endoscope from the body tissue through the transparent tip during tissue penetration. Another trocar which has similar features is described in U.S. Pat. No. 5,441,041.

While safety is a significant concern in connection with the design of trocars, so is cost and surgical waste generated from the use of disposable trocars. Accordingly, multipatient use trocars have become popular and are now being described in the patent literature. For example, U.S. Pat. Nos. 5,383,860; 5,496,280 and 5,549,565 describe trocars which have reusable cannulas adapted for multiple patient use coupled to cannula housings where the entire housing or a portion of the housing is disposed of and replaced after a single patient use. U.S. Pat. No. 5,256,147 describes a reusable trocar which has an obturator with a replaceable tip portion. The ability to reuse trocar assemblies saves hospital money, and as pressure increases to reduce and minimize hospital costs, alternatives which these trocars exemplify are becoming more attractive to hospital personnel.

The ability to minimize surgical waste is also possible by varying the way in which surgical components are packaged and distributed to end users. For example, U.S. Pat. No. 5,144,942 describes a surgical kit which includes a plurality of trocar cannulas for each trocar obturator in the kit package. The obturator can be used with each of the cannula sleeves to provide numerous access ports during minimally invasive surgery without the need to package a trocar obturator with each cannula sleeve. Another kit patent which describes a combination of shielded and non-shielded trocar assemblies is U.S. Pat. No. 5,453,094.

Although safety, cost and reduction in packaging contents to reduce surgical waste have all been factors which have been considered in the design and packaging of trocars, there are problems which still need to be addressed. Specifically, what is needed is a trocar assembly which can provide visualization concurrently with tissue penetration, and is adapted for multi-patient use at lower cost. In particular, it would be desirable if a trocar assembly providing for visualization could be fabricated which has a reusable obturator for use on multiple patients to lower cost. Further, it would be particularly desirable if such a trocar assembly could be fabricated which is convenient and easy to use.

SUMMARY OF THE INVENTION

The invention is a multi-patient use trocar assembly for providing access to surgical sites within body cavities of multiple patients during minimally invasive surgical procedures. The trocar assembly comprises two subassemblies. The subassemblies are an obturator subassembly and a cannula subassembly.

The obturator subassembly has an elongated obturator shaft, a first obturator tip and an obturator grip. The elongated obturator shaft has proximal and distal ends and an opening in the shaft adjacent the shaft distal end for receiving an endoscope. The obturator shaft is reusable and adapted for use on multiple patients.

The first obturator tip is detachably mounted onto the distal end of the obturator shaft. The tip extends distally from the shaft distal end. The first obturator tip is transparent. The first obturator tip is capable of transmitting illuminated images provided by the endoscope from the body cavity through the transparent tip. It is shaped to enlarge an opening through a body wall as the trocar assembly is advanced toward any one of the surgical sites. The first obturator tip is disposable following use on a first patient.

The obturator grip is attached to the proximal end of the obturator shaft. It facilitates the manipulation of the obturator subassembly.

The cannula subassembly removably receives the obturator subassembly. The cannula subassembly has a cannula housing and an elongated cannula tube attached to the cannula housing. The cannula tube surrounds the obturator shaft of the obturator subassembly when the obturator shaft is received in the cannula subassembly.

Following use of the trocar assembly to provide access for the first patient, the first obturator tip is removed from the distal end of the obturator shaft. The first obturator tip is disposed of, and a second obturator tip is mounted on the shaft distal end for use of the trocar subassembly to provide access for a second patient.

The trocar assembly of this invention has a reusable obturator shaft for multi-patient use, and a disposable transparent obturator tip which is detached from the distal end of the obturator shaft following a single patient use. A second transparent tip can then be attached to the reusable obturator shaft, and the trocar assembly can be used to provide access to the surgical site of the second patient. Since the obturator shaft is reusable, and the disposable transparent obturator tip is detachable, the trocar assembly can be used to provide access for multiple patients without the need to dispose of the entire trocar assembly. Instead, only the transparent obturator tip needs to be disposed of and replaced, and the rest of the trocar assembly can be used again.

Accordingly, the trocar assembly of this invention provides for visualization concurrently with tissue penetration when used in combination with an endoscope for the transmission of illuminated images from the body cavity through the transparent obturator tip. It provides for visualization at a cost significantly lower than similarly featured trocar assemblies described in the patent literature. Furthermore, the trocar assembly of this invention is easy and convenient to use.

The trocar of this invention is especially useful during a minimally invasive surgical procedure where an access port is needed to provide a passageway for the insertion and withdrawal of endoscopic instruments. However, the trocar assembly can be used in open surgical procedures as well.

BRIEF DESCRIPTION OF THE PREFERRED EMBODIMENTS

DETAILED DESCRIPTION OF THE PREFERRED EMBODIMENTS

Figure 1:
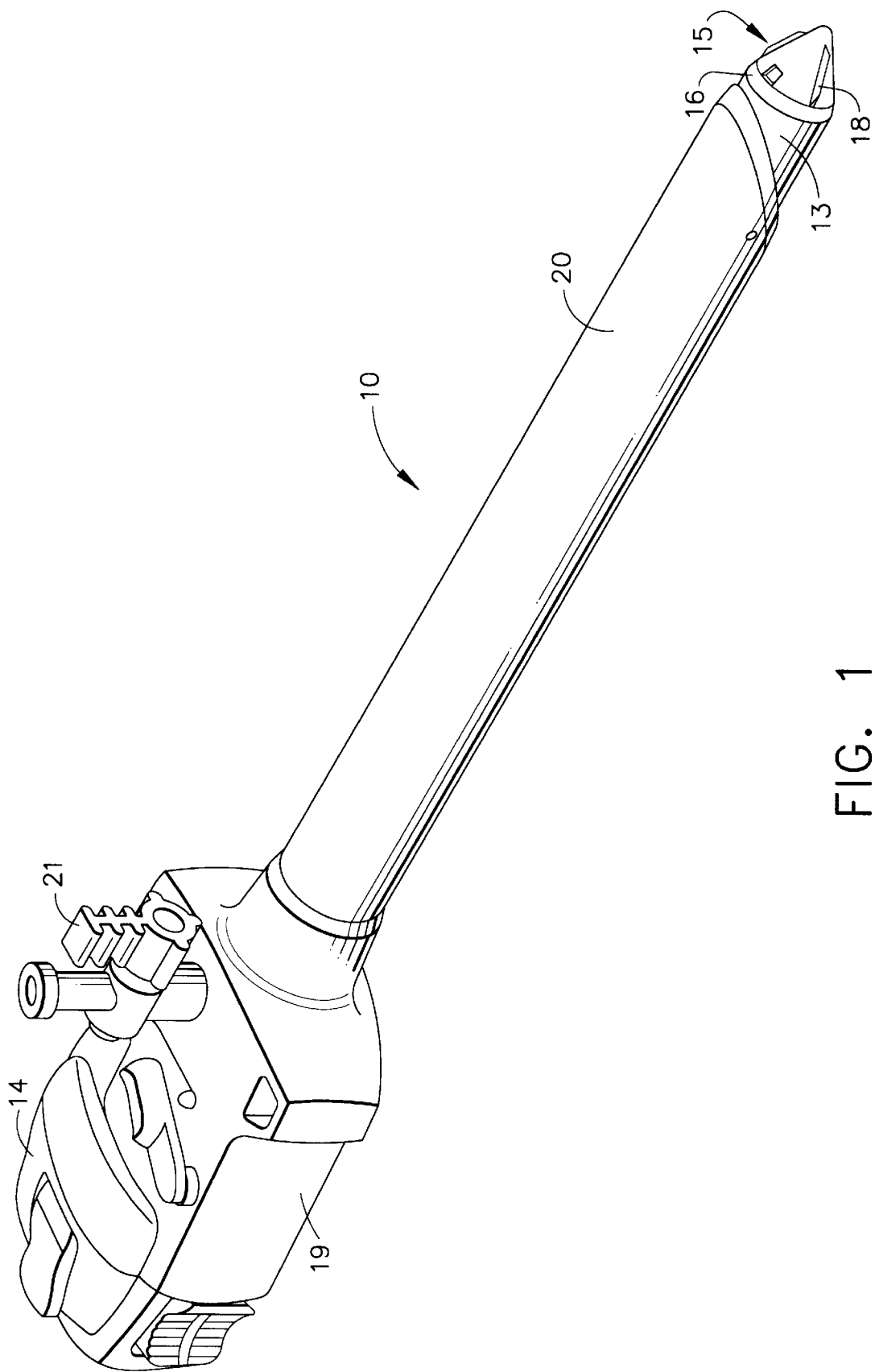
FIG. 1 is a perspective view of a preferred multi-patient use trocar assembly of this invention.
Figure 2:
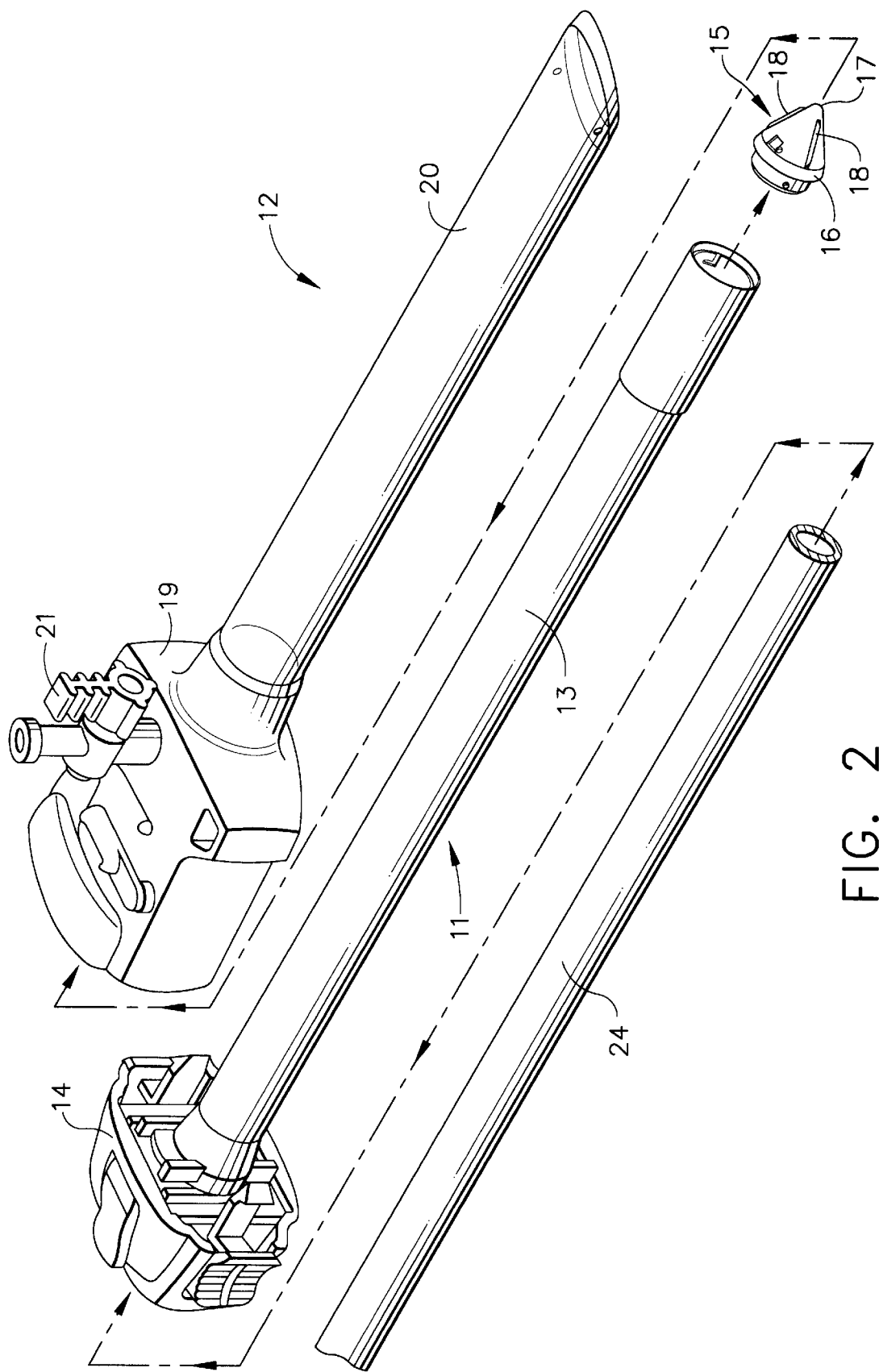
FIG. 2 is an exploded perspective view of the trocar assembly of FIG. 1 illustrating the detachable mounting of the disposable obturator tip to the reusable shaft of the obturator subassembly, and further illustrating the trocar assembly in cooperation with an endoscope.

A preferred trocar assembly 10 of this invention particularly configured for providing access ports during minimally invasive surgery on multiple patients in an economically efficient manner is illustrated in FIGS. 1 and 2. The trocar assembly has two interfitting subassemblies. The obturator subassembly 11 penetrates or dissects through the tissue layers of the patient to provide an opening adjacent the surgical site. The cannula subassembly 12 provides the access portal for insertion and withdrawal of various surgical instruments through the opening created by the penetration or dissection of the tissue layers with the obturator subassembly.

The obturator subassembly 11 has three primary components. It has a long, hollow obturator shaft 13. The shaft is rigid to withstand the force exerted on the tissue layers when penetration or dissection through the tissue is performed.

The shaft is composed of a material which enables the reuse of the obturator shaft on multiple patients. Advantageously, the reusable shaft is composed of a metal such as stainless steel, aluminum or titanium, or a plastic such as a polysulfone or a plastic sold by General Electric under the trademark ULTEM. Preferably, the reusable shaft is composed of stainless steel. At the proximal end of the obturator shaft 13, there is affixed an obturator grip 14 for manipulating the obturator subassembly. At the distal end of the obturator shaft, a first obturator tip 15 is detachably mounted to the shaft distal end (the specific details illustrating how the obturator tip is detachably mounted to the shaft distal end are discussed in connection with FIGS. 4–7 below). The obturator tip facilitates the penetration or dissection of the tissue layers as the trocar assembly is inserted through the tissue layers toward the surgical site, and is therefore shaped to enlarge an opening in the tissue as the trocar assembly is inserted toward the internal surgical site.

In contrast to the reusable obturator shaft, the obturator tip 15 is composed of a disposable material. Accordingly, following the use of the trocar assembly on a first patient, the first obturator tip is detached from the shaft distal end, the first obturator tip is disposed of, and a second disposable obturator tip is then mounted onto the shaft distal end so that the obturator subassembly can be reused on a second surgical patient. Furthermore, the obturator tip is composed of a transparent material so that the obturator tip acts as a transparent window enabling concurrent visualization during penetration or dissection when an endoscope is used, as discussed in more detail below.

The obturator tip 15 preferably has a conical configuration to facilitate the penetration or dissection of tissue. The conical tip has a tip base 16 with a base diameter substantially equivalent to that of the shaft diameter. At the opposite end of the obturator tip, spaced from the tip base, is an apex 17. Lastly, a pair of blunt-edged blades 18, or tissue separators, spaced 180° from each other, extend from the surface of the obturator tip to further facilitate the penetration or dissection of tissue.

Advantageously, the disposable obturator tip is composed of rigid plastic such as a polycarbonate, co-polyester or acrylic. The preferred material of construction for the disposable obturator tip is co-polyester.

The cannula subassembly 12 of the trocar assembly 10 has a cannula housing 19 and an elongated cannula tube 20 extending from the housing. The cannula housing has a stopcock 21 for the selective passage of a pressurizing fluid such as carbon dioxide to insufflate the body cavity during a minimally invasive surgical procedure, if desired. The elongated cannula tube receives the obturator shaft 13 when the obturator subassembly is inserted into and through the cannula housing and tube. When inserted, the obturator grip 14 can be latched onto the cannula housing 19. The disposable obturator tip 15, and a portion of the distal end of the reusable obturator shaft, extend from the distal end of the cannula tube when the obturator grip is latched onto the cannula housing.

Figure 3:
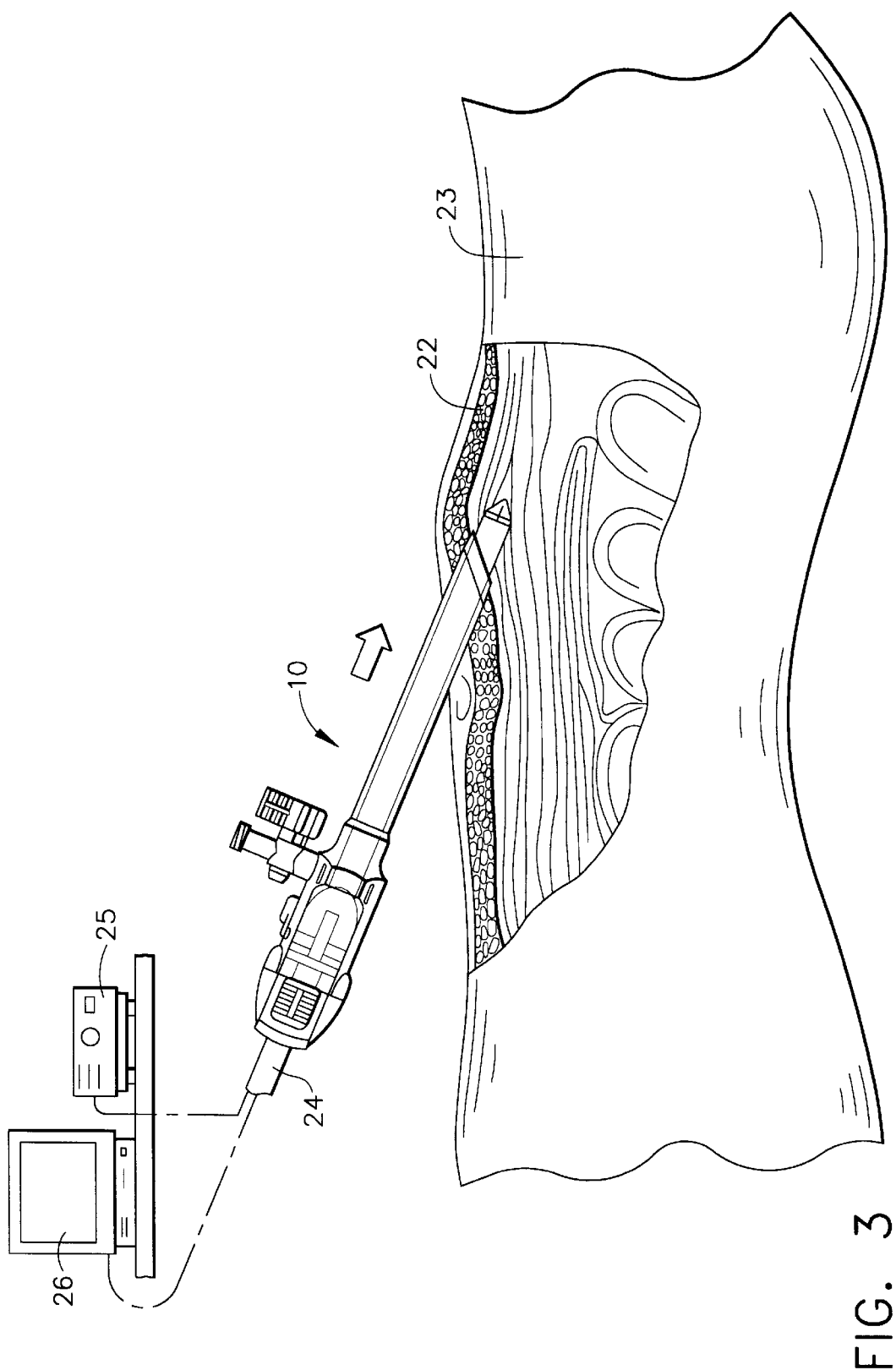
FIG. 3 is a side elevational environmental view partially in section illustrating the use of the trocar assembly of FIG. 1 in combination with an endoscope.

When a first obturator tip is mounted onto the shaft distal end, and the obturator subassembly is inserted fully through the cannula subassembly so that the cannula tube receives the obturator shaft and the obturator grip is latched onto the cannula housing, the trocar assembly is now ready for the penetration or dissection of tissue on a first patient while providing simultaneous visualization as the tissue is penetrated or dissected. As illustrated in FIG. 3, the trocar assembly is advanced in the direction illustrated by the arrow through various tissue layers 22 of a first surgical patient 23. A conventional endoscope 24 (depicted in FIG. 2) can be inserted through the hollow obturator shaft of the obturator subassembly so that the endoscope is positioned adjacent the proximal end of the transparent obturator tip. The endoscope is connected to a light source 25 to provide illumination through the transparent obturator tip to the surgical site. It is also connected to a video monitor 26 to display the illuminated images transmitted from the surgical site. In this way, the surgeon can readily monitor the advance of the trocar assembly through the tissue layers from the video monitor.

When the advancement of the trocar assembly is completed on the first patient, the obturator subassembly and the endoscope may be removed from the cannula subassembly. An access portal is therefore provided through the cannula tube of the cannula subassembly so that additional instrumentation can then be inserted and withdrawn through the cannula subassembly to the surgical site to complete a desired surgical procedure on the first patient. When the surgical procedure is completed on the first patient, the disposable obturator tip can be detached from the obturator shaft, a second obturator tip can be subsequently attached to the obturator shaft, and the trocar assembly (with or without a new cannula subassembly) can be used on a second patient after appropriate cleaning and sterilization. In this manner, the trocar assembly can be used on multiple patients while enjoying the economic advantages attendant with the ability to reuse the obturator shaft.

Figure 4:
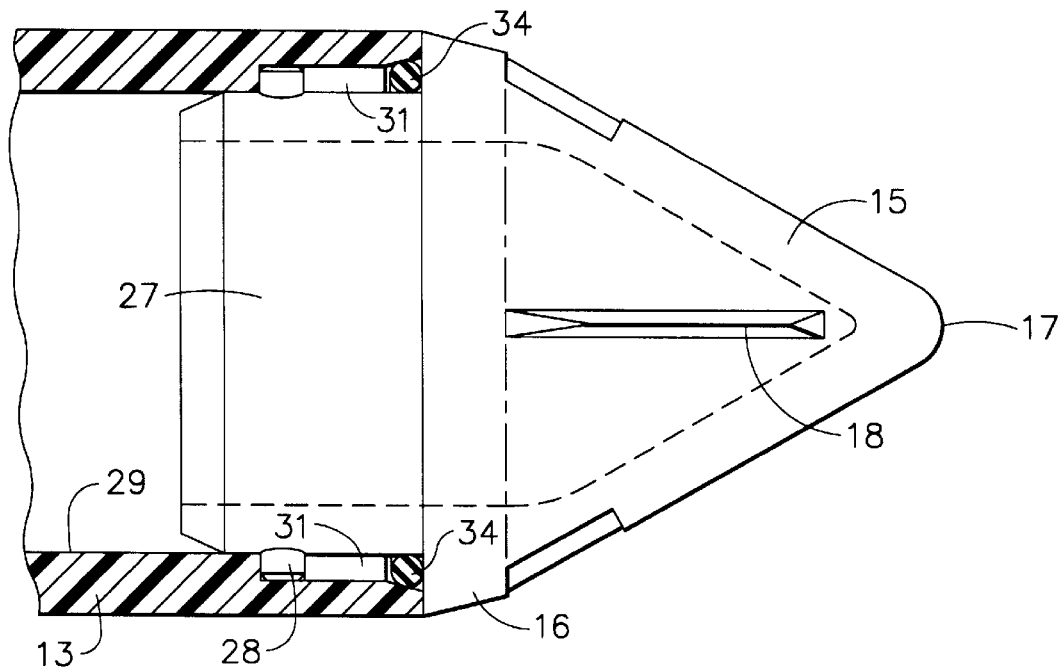
FIG. 4 is a side elevational view of the preferred disposable obturator tip in cooperation with a fragmentary sectional view of a reusable obturator shaft, particularly illustrating a preferred embodiment for detachably mounting the obturator tip to the obturator shaft.
Figure 5:
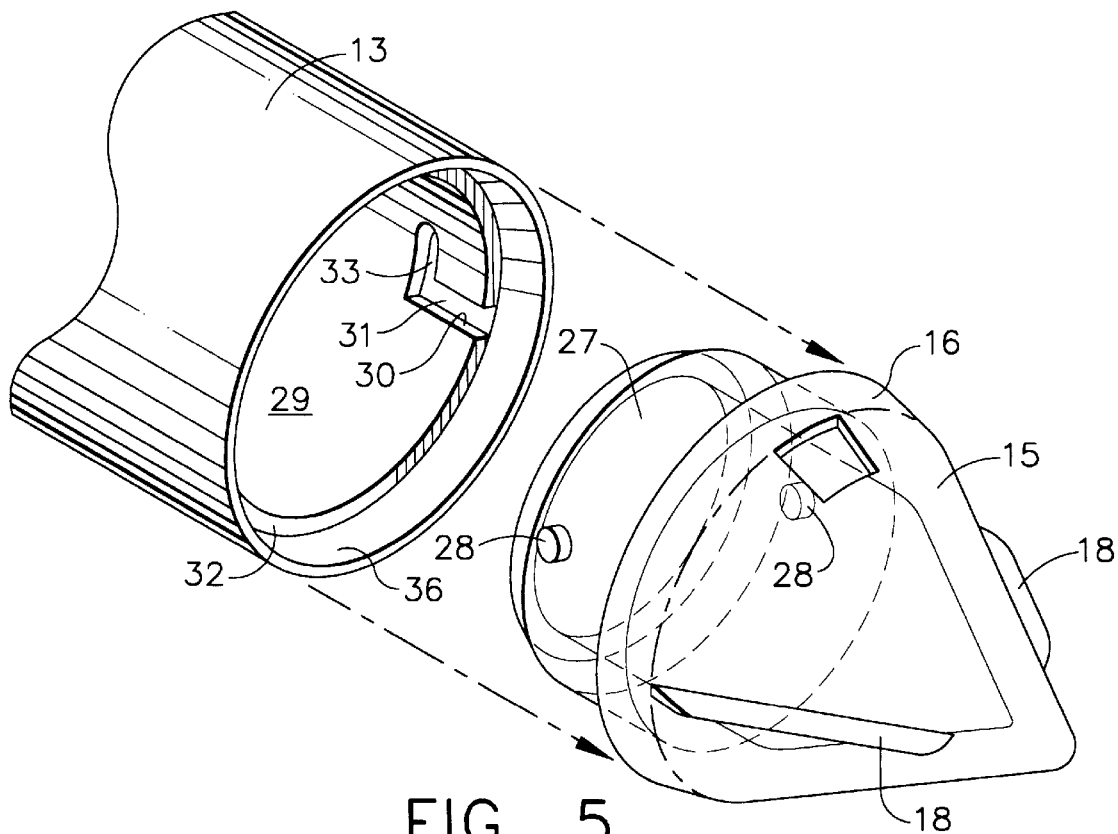
FIG. 5 is an exploded perspective view further illustrating the mounting of the tip to the shaft as shown in FIG. 4.
Figure 6:
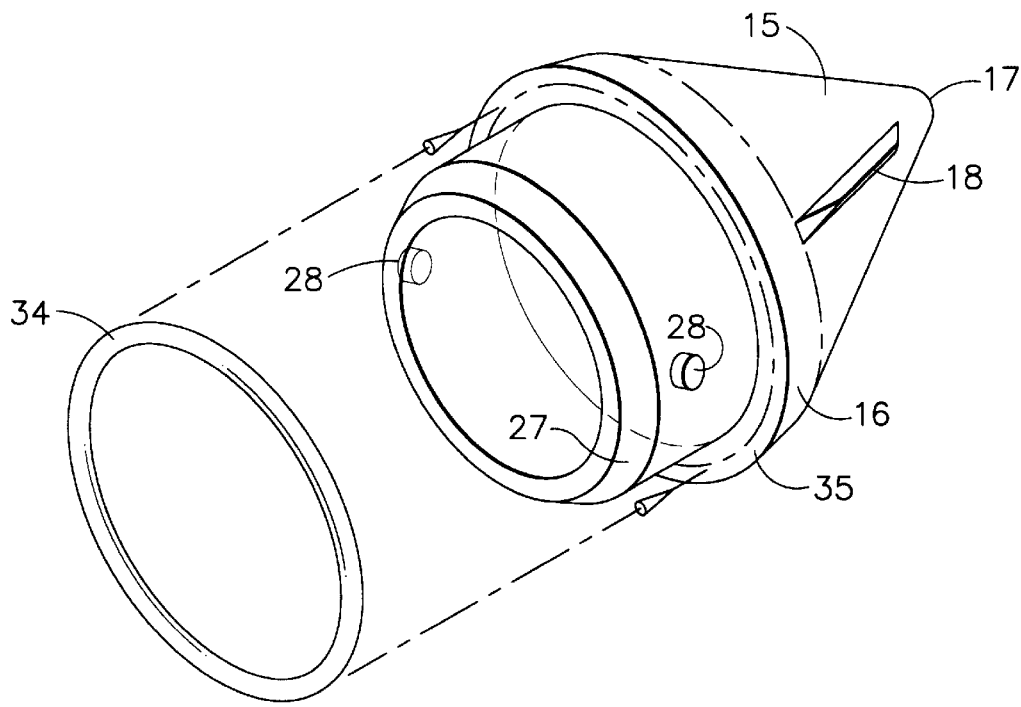
FIG. 6 is a perspective view of the obturator tip illustrated in FIGS. 4 and 5 in combination with a preferred tip seal.

FIGS. 4–6 illustrate a first preferred embodiment of the structure for detachably mounting the disposable obturator tip 15 to the distal end of the obturator shaft. The obturator tip has an annulus 27 descending from the base 16 of the obturator tip. When attached to the shaft distal end, the annulus descends through the interior of the shaft distal end. The annulus has a pair of attachment pins 28 extending from the annulus wall and spaced about 180° from each other. Correspondingly, the inner wall 29 of the obturator shaft at the distal end of the obturator shaft has a pair of receiving slots 30 for receiving the attachment pins extending from the interior annulus of the obturator tip. Each of the receiving slots has a longitudinal channel section 31 descending proximally from a distal edge surface 32 at the shaft distal end, and a circumferential slot section 33 spaced from the distal edge surface of the obturator shaft (only one of the circumferential slot sections is illustrated in FIG. 5). The mounting mechanism can, therefore, be best viewed as a "twist-lock" mechanism because when the surgeon or operating room assistant wants to mount the obturator tip to the shaft distal end, he initially guides the attachment pins through the longitudinal channel section of the receiving slots, and then twists the obturator tip to guide the pins through the circumferential slot sections to secure the obturator tip to the shaft distal end. When the surgeon or operating room assistant wants to remove the tip from the shaft distal end, the procedure is simply reversed.

In a particularly preferred embodiment, a sealing structure is provided between the obturator tip and the shaft distal end to prevent the leakage of insufflation gas through the trocar assembly or bodily fluids from penetrating into the interior space of the transparent obturator tip, thus interfering with optimum visual acuity during use. Of course, the sealing structure facilitates the attachment and detachment of the transparent obturator tip. An "O" ring elastomeric seal 34 is fitted between a seal stop 35 located on the underside of the tip base of the obturator tip, and the distal edge surface 32 of the obturator shaft. As a way of advantageously distributing the pressure exerted on the seal when the obturator tip is attached to the shaft distal end, a seal chamfer 36 extends from the distal edge surface of the obturator shaft.

Figure 7:
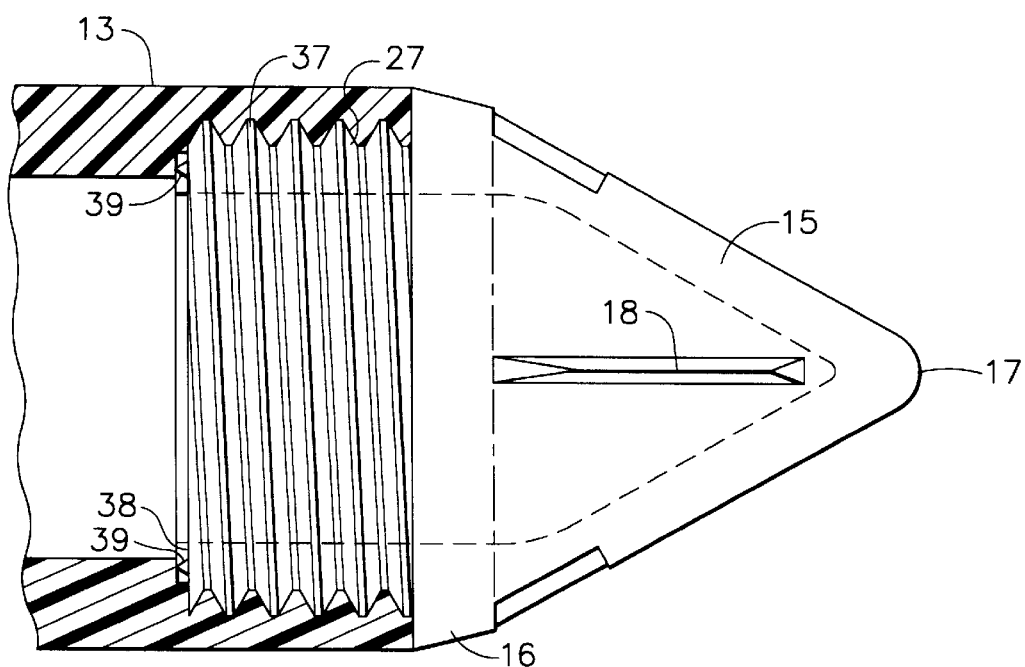
FIG. 7 is a side elevational view of the preferred obturator tip in cooperation with a fragmentary sectional view of a reusable obturator shaft illustrating another preferred embodiment for detachably mounting and sealing the obturator tip to the shaft.

Another embodiment of a preferred structure for detachably mounting the transparent obturator tip to the shaft distal end is illustrated in FIG. 7. A simple mating threaded attachment 37 is provided between the interior annulus 27 descending from the tip base 16 of the obturator tip 15, and the shaft distal end. The interior annulus of the obturator tip is threaded, and the distal end of the obturator shaft has mating threads to receive the threaded annulus. A seal ring or washer 38 is integrally attached to the proximal end of the threaded annulus of the obturator tip. The integral ring has a deformable ring apex which is deformed when the obturator tip is screwed into the shaft distal end, and the ring apex 39 of the seal ring bears upon the distal edge surface of the obturator shaft.

Figure 8:
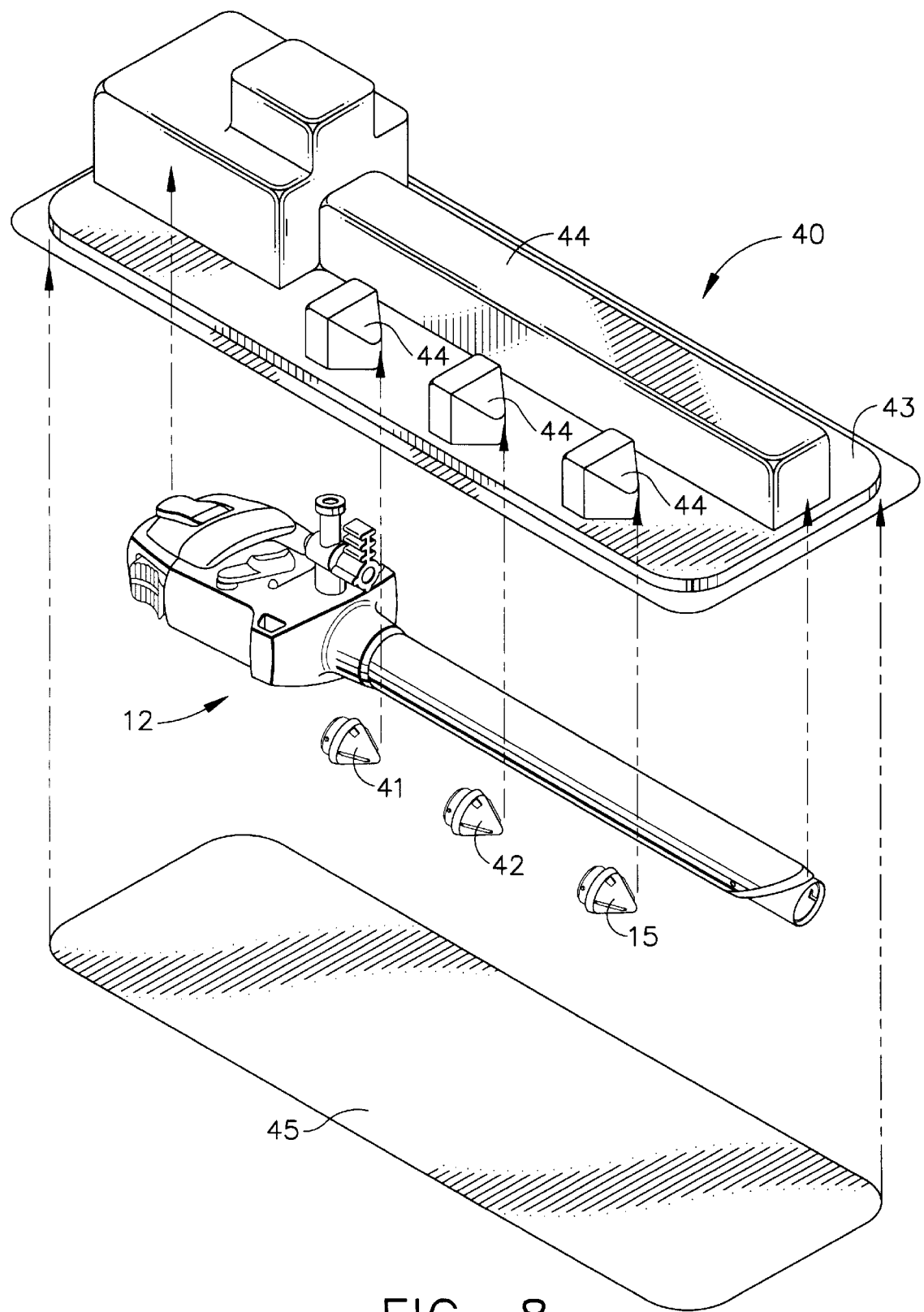
FIG. 8 is an exploded package assembly illustrating a surgical kit which contains a trocar assembly and first, second and third disposable obturator tips.
Figure 9:
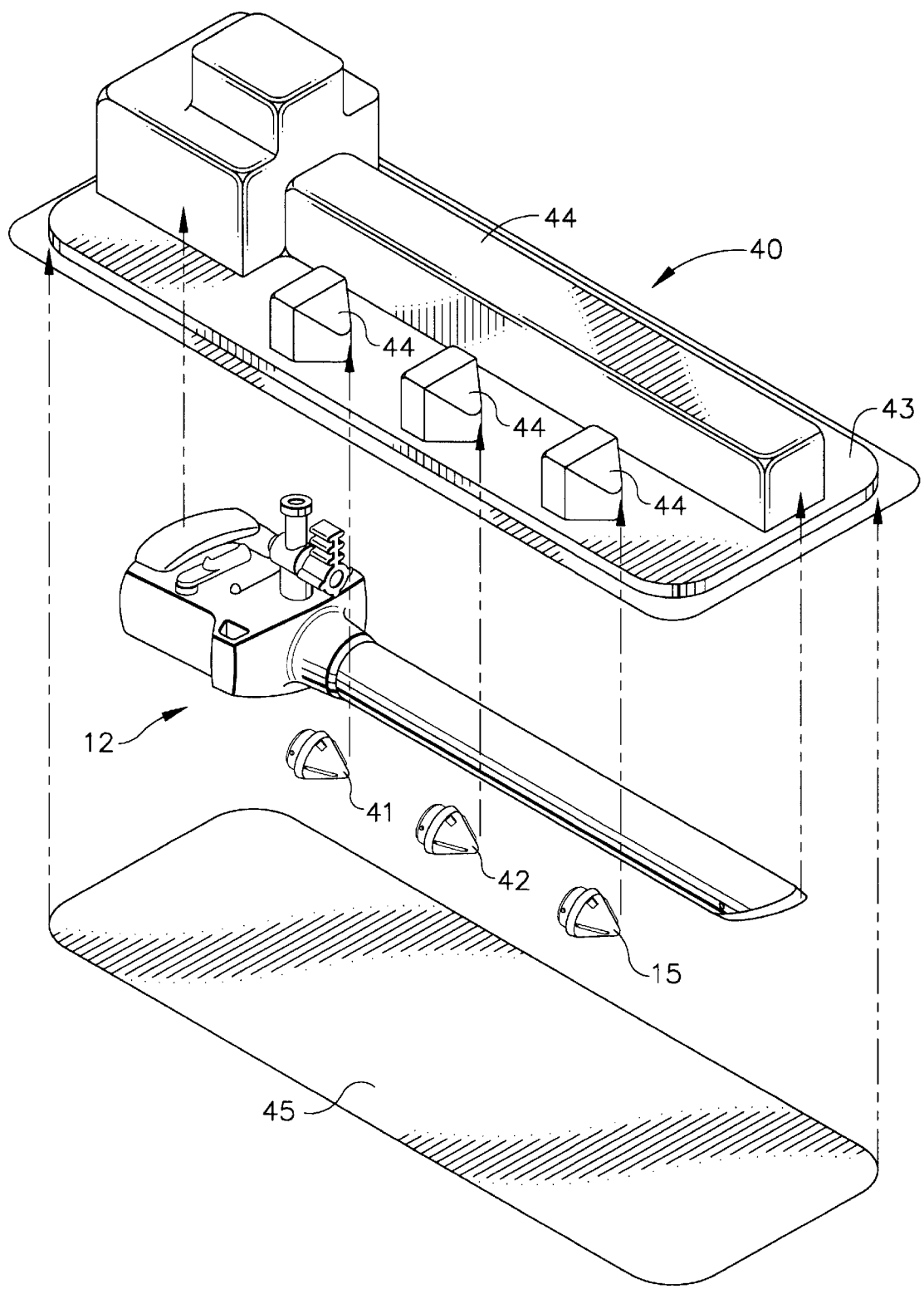
FIG. 9 is an exploded package assembly illustrating a surgical kit containing a cannula subassembly and three disposable obturator tips.

Referring now to FIGS. 8 and 9, there are shown packaging options to take advantage of the unique features of the trocar assembly of this invention. FIG. 8 illustrates a packaging enclosure 40 which includes the preferred trocar assembly 10 of this invention with its first transparent, disposable obturator tip 15. Significantly, also included in the packaging enclosure are second and third disposable transparent obturator tips, 41 and 42, respectively. The trocar assembly and the obturator tips are packaged as a single package enclosure in a surgical kit. The surgical kit includes a bottom shipping tray 43 containing multiple cavities 44 therein for receiving the various components of the kit. It also includes a top lid 45 which is affixed over the bottom shipping tray to provide an integrated packaging unit for a surgical kit. In another packaging configuration particularly illustrated in FIG. 9, the integrated packaging enclosure 40 of the surgical kit contains the cannula subassembly 12 of the trocar assembly and the first, second and third disposable obturator tips. Advantageously, in this embodiment, the reusable obturator shaft which is purchased with an initial purchase of a trocar assembly can be reused on multiple patients, and a kit simply containing a cannula subassembly of the disposable obturator kits can be purchased to provide a fully integrated trocar assembly. When this kit configuration is used, as well as other kit configurations taking advantage of the reusable nature of the obturator shaft and disposability of the obturator tips and cannula subassemblies, it is unnecessary to purchase the entire trocar assembly for each access portal desired. Therefore, instrumentation costs are lowered and the packaging waste is minimized.

In another embodiment of the invention, a kit which contains a plurality of transparent obturator tips is provided in a single package enclosure. This is particularly advantageous when not only the obturator shaft is reusable, but also the cannula subassembly as well.

Although this invention has been described in connection with its most preferred embodiments, numerous additional embodiments can be readily envisioned by those skilled in this art. For example, those skilled in this art can readily envision numerous additional attachment mechanisms for detachably mounting the disposable obturator tip to the reusable obturator shaft. Likewise, numerous surgical kit configurations providing an integrated packaging enclosure which utilizes the unique features of the trocar assembly of this invention can be readily envisioned by those skilled in this art. Accordingly, the reader should recognize that the scope of this invention is not in any way limited to the specific embodiments described in this detailed description, but rather is defined by the claims which appear below.

What is claimed is:

1. A multi-patient use trocar assembly for providing access to surgical sites within body cavity of multiple patients during minimally invasive surgical procedures, said assembly comprising:

an obturator subassembly having (i) an elongated obturator shaft with proximal and distal ends and an opening therein adjacent said shaft distal end for receiving an endoscope, said obturator shaft being reusable and adapted for use on said multiple patients, (ii) a first obturator tip detachably mounted onto said shaft distal end and extending distally therefrom, said first obturator tip being transparent for transmitting illuminated images provided by said endoscope from the body cavity through said transparent tip, said first obturator tip shaped to enlarge an opening through a body wall as said trocar assembly is advanced toward any of said surgical sites, and said first obturator tip being disposable following use on a first patient, (iii) an obturator grip attached to said obturator shaft proximal end for facilitating manipulation of said obturator subassembly, and (iv) a seal mounted adjacent said shaft distal end for facilitating attachment and detachment of said first obturator tip; and a cannula subassembly for removably receiving said obturator subassembly, said cannula subassembly having (i) a cannula housing, and (ii) an elongated cannula tube attached to said cannula housing, said cannula tube surrounding said obturator shaft when said obturator shaft is received in said cannula subassembly.

2. The trocar assembly of claim 1 wherein said elongated obturator shaft has a longitudinal axis and an outside diameter, and each of said first and second obturator tips has a tip base adjacent said shaft distal end, said tip base having a base diameter about equal to said outside diameter of said obturator shaft.

3. The trocar assembly of claim 2 wherein each of said first and second obturator tips is symmetrical about the longitudinal axis of said obturator shaft.

4. The trocar assembly of claim 3 wherein each of said first and second obturator tips has an apex spaced from said tip base.

5. The trocar assembly of claim 4 wherein each of said first and second obturator tips is a conical tip.

6. The trocar assembly of claim 2 wherein each of said first and second obturator tips has an annulus descending from said tip base of each of said tips, and when each of said tips is attached to said shaft distal end, said annulus is located interiorly of said shaft distal end.

7. The trocar assembly of claim 6 wherein said annulus has a pair of attachment pins extending therefrom.

8. The trocar assembly of claim 7 wherein said obturator shaft has an inner wall, and said inner wall has a pair of receiving slots for receiving said attachment pins extending from said annulus of each of said obturator tips so as to detachably mount each of said tips to said shaft distal end.

9. The trocar of claim 8 wherein said shaft distal end has a distal edge surface, and each of said receiving slots has a longitudinal channel section descending proximally from said distal edge surface, and a circumferential slot section spaced from said distal edge surface.

10. The trocar assembly of claim 2 wherein said seal is fitted between said shaft distal end and said tip base of each said first and second obturator tips.

11. The trocar assembly of claim 10 wherein said seal is an "O" ring elastomeric seal.

12. The trocar assembly of claim 11 wherein said shaft distal end has a distal edge surface, said tip base has a seal stop located on an underside surface of said tip base, and said "O" ring seal is fitted between said distal edge surface and said seal stop.

13. The trocar assembly of claim 6 wherein said annulus descending from said tip base and said shaft distal end have mating threads for detachably threading each of said obturator tips to said shaft distal end.

14. The trocar assembly of claim 13 wherein said seal is integrally attached to said threaded annulus descending from said tip base.

15. The trocar assembly of claim 14 wherein said seal has a deformable ring apex thereon.

16. A method for providing access to surgical sites within body cavities of multiple patients during minimally invasive surgical procedures, said method comprising:

a) providing a multi-patient use trocar assembly which includes:

an obturator subassembly having (i) an elongated obturator shaft with proximal and distal ends and an opening therein adjacent said shaft distal end for receiving an endoscope, said obturator shaft being reusable and adapted for use on said multiple patients, (ii) a first obturator tip detachably mounted onto said shaft distal end and extending distally therefrom, said first obturator tip being transparent for transmitting illuminated images provided by said endoscope from the body cavity through said transparent tip, said first obturator tip shaped to enlarge an opening through a body wall as said trocar assembly is advanced toward any of said surgical sites, and said first obturator tip being disposable following use on a first patient, and (iii) an obturator grip attached to said obturator shaft proximal end for facilitating manipulation of said obturator subassembly; and a cannula subassembly for removably receiving said obturator subassembly, said cannula subassembly having (i) a cannula housing, and (ii) an elongated cannula tube attached to said cannula housing, said cannula tube surrounding said obturator shaft when said obturator shaft is received in said cannula subassembly;

b) using said trocar assembly to provide access for said first patient;

c) removing said first obturator tip from said shaft distal end for disposal thereof following use of said trocar assembly to provide access for said first patient;

d) mounting a second obturator tip on said shaft distal end; and e) using said trocar assembly with said second obturator tip mounted on said shaft distal end to provide access for said second patient.

* * * * *